United States Patent
Warren et al.

(10) Patent No.: US 9,764,152 B2
(45) Date of Patent: *Sep. 19, 2017

(54) MULTIPLE ELECTRODE VECTORS FOR IMPLANTABLE CARDIAC TREATMENT DEVICES

(71) Applicant: CAMERON HEALTH INC, St. Paul, MN (US)

(72) Inventors: Jay A. Warren, San Juan Capistrano, CA (US); Gust H. Bardy, Carnation, WA (US)

(73) Assignee: Cameron Health, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/138,674

(22) Filed: Apr. 26, 2016

(65) Prior Publication Data

US 2016/0235998 A1 Aug. 18, 2016

Related U.S. Application Data

(60) Continuation of application No. 14/452,859, filed on Aug. 6, 2014, now Pat. No. 9,345,899, which is a
(Continued)

(51) Int. Cl.
*A61N 1/00* (2006.01)
*A61N 1/39* (2006.01)
(Continued)

(52) U.S. Cl.
CPC ............ *A61N 1/3925* (2013.01); *A61B 5/042* (2013.01); *A61B 5/04011* (2013.01);
(Continued)

(58) Field of Classification Search
CPC .. A61N 1/3621–1/3624; A61N 1/3686; A61N 1/3956; A61B 5/04011; A61B 5/046–5/0472
See application file for complete search history.

(56) References Cited

U.S. PATENT DOCUMENTS 4,550,502 A 11/1985 Grayzel
4,589,420 A 5/1986 Adams et al.
(Continued)

FOREIGN PATENT DOCUMENTS

EP 0813889 A2 12/1997
EP 1184050 A2 3/2002
(Continued)

OTHER PUBLICATIONS

"U.S. Appl. No. 10/901,258, Response filed Jul. 24, 2007 to Restriction Requirement mailed Jun. 25, 2007", 9 pgs.
(Continued)

*Primary Examiner* — Scott Getzow
(74) *Attorney, Agent, or Firm* — Seager, Tufte & Wickhem LLP

(57) ABSTRACT

The implantable cardiac treatment system of the present invention is capable of choosing the most appropriate electrode vector to sense within a particular patient. In certain embodiments, the implantable cardiac treatment system determines the most appropriate electrode vector for continuous sensing based on which electrode vector results in the greatest signal amplitude, or some other useful metric such as signal-to-noise ratio (SNR). The electrode vector possessing the highest quality as measured using the metric is then set as the default electrode vector for sensing. Additionally, in certain embodiments of the present invention, a next alternative electrode vector is selected based on being generally orthogonal to the default electrode vector. In yet other embodiments of the present invention, the next alternative electrode vector is selected based on possessing the next highest quality metric after the default electrode vector. In some embodiments, if analysis of the default vector is ambiguous, the next alternative electrode vector is analyzed to reduce ambiguity.

20 Claims, 8 Drawing Sheets

Related U.S. Application Data continuation of application No. 12/144,462, filed on Jun. 23, 2008, now Pat. No. 8,825,157, which is a division of application No. 10/901,258, filed on Jul. 27, 2004, now Pat. No. 7,392,085.

(60) Provisional application No. 60/490,779, filed on Jul. 28, 2003.

(51) Int. Cl.
| | |
|---|---|
| A61B 5/0424 | (2006.01) |
| A61N 1/362 | (2006.01) |
| A61B 5/00 | (2006.01) |
| A61N 1/37 | (2006.01) |
| A61B 5/04 | (2006.01) |
| A61B 5/042 | (2006.01) |

(52) U.S. Cl.
CPC .......... *A61B 5/0424* (2013.01); *A61B 5/7203* (2013.01); *A61B 5/7207* (2013.01); *A61N 1/3622* (2013.01); *A61N 1/3706* (2013.01); *A61N 1/3987* (2013.01)

(56) References Cited

U.S. PATENT DOCUMENTS

| | | |
|---|---|---|
| 5,137,025 A | 8/1992 | Turner, II |
| 5,331,966 A | 7/1994 | Bennett et al. |
| 5,501,702 A | 3/1996 | Plicchi et al. |
| 5,558,098 A | 9/1996 | Fain |
| 5,645,070 A | 7/1997 | Turcott |
| 5,707,398 A | 1/1998 | Lu |
| 5,999,853 A | 12/1999 | Stoop et al. |
| 6,029,086 A | 2/2000 | Kim et al. |
| 6,044,297 A | 3/2000 | Sheldon et al. |
| 6,312,388 B1 | 11/2001 | Marcovecchio et al. |
| 6,496,715 B1 | 12/2002 | Lee et al. |
| 6,647,292 B1 | 11/2003 | Bardy et al. |
| 6,721,597 B1 | 4/2004 | Bardy et al. |
| 6,731,978 B2 | 5/2004 | Olson et al. |
| 6,754,528 B2 | 6/2004 | Bardy et al. |
| 6,892,092 B2 | 5/2005 | Palreddy et al. |
| 7,020,523 B1 | 3/2006 | Lu et al. |
| 7,130,689 B1 | 10/2006 | Turcott |
| 7,177,689 B2 | 2/2007 | Ternes et al. |
| 7,181,281 B1 | 2/2007 | Kroll |
| 7,248,921 B2 | 7/2007 | Palreddy et al. |
| 7,330,757 B2 | 2/2008 | Ostroff et al. |
| 7,379,772 B2 | 5/2008 | Bardy et al. |
| 7,392,085 B2 | 6/2008 | Warren et al. |
| 7,412,287 B2 | 8/2008 | Yonce et al. |
| 7,627,367 B2 | 12/2009 | Warren et al. |
| 8,825,157 B2 | 9/2014 | Warren et al. |
| 2002/0169484 A1 | 11/2002 | Mathis et al. |
| 2005/0192507 A1 | 9/2005 | Warren et al. |
| 2007/0123947 A1 | 5/2007 | Wenger et al. |
| 2008/0269813 A1 | 10/2008 | Greenhut et al. |
| 2008/0275521 A1 | 11/2008 | Warren et al. |
| 2009/0093731 A1 | 4/2009 | Palreddy et al. |

FOREIGN PATENT DOCUMENTS

| | | |
|---|---|---|
| EP | 1745741 A1 | 1/2007 |
| WO | 03020367 A1 | 3/2003 |
| WO | 2004105871 A1 | 12/2004 |
| WO | 2007089959 A1 | 8/2007 |

OTHER PUBLICATIONS

"U.S. Appl. No. 10/901,258, Restriction Requirement mailed Jun. 25, 2007", 5 pgs.
"International Application Serial No. PCT/US2001/029106, International Search Report mailed Mar. 21, 2002", 4 pgs.
"International Application Serial No. PCT/US2001/029106, Written Opinion mailed Sep. 3, 2002", 6 pgs.
"International Application Serial No. PCT/US2001/029168, International Search Report mailed Mar. 26, 2002", 5 pgs.
"International Application Serial No. PCT/US2001/029168, Written Opinion mailed Sep. 10, 2002", 7 pgs.
"U.S. Appl. No. 10/856,084, filed May 27, 2004", 120 pgs.
"U.S. Appl. No. 10/863,599 filed Jun. 8, 2004", 42 pgs.
"U.S. Appl. No. 10/901,258, Non Final Office Action mailed Sep. 26, 2007", 6 pgs.
"U.S. Appl. No. 10/901,258, Response filed Dec. 24, 2007 to Non Final Office Action mailed Sep. 26, 2007", 13 pgs.
"U.S. Appl. No. 11/120,284, Final Office Action mailed Jul. 28, 2008", 5 pgs.
"U.S. Appl. No. 11/120,284, Non Final Office Action mailed Jan. 12, 2009", 6 pgs.
"U.S. Appl. No. 11/120,284, Non Final Office Action mailed Feb. 1, 2008", 6 pgs.
"U.S. Appl. No. 11/120,284, Response filed Apr. 9, 2009 to Non Final Office Action mailed Jan. 12, 2009", 11 pgs.
"U.S. Appl. No. 11/120,284, Response filed May 1, 2008 to Non Final Office Action mailed Feb. 1, 2008", 17 pgs.
"U.S. Appl. No. 11/120,284, Response filed Oct. 28, 2008 to Final Office Action mailed Jul. 28, 2008", 9 pgs.
"U.S. Appl. No. 12/144,462, Advisory Action mailed Jun. 3, 2011", 3 pgs.
"U.S. Appl. No. 12/144,462, filed Jun. 23, 2008", 27 pgs.
"U.S. Appl. No. 12/144,462, Final Office Action mailed Mar. 25, 2011", 5 pgs.
"U.S. Appl. No. 12/144,462, Non Final Office Action mailed Oct. 19, 2010", 7 pgs.
"U.S. Appl. No. 12/144,462, Non Final Office Action mailed Nov. 29, 2013", 6 pgs.
"U.S. Appl. No. 12/144,462, Notice of Allowance mailed Apr. 29, 2014", 5 pgs.
"U.S. Appl. No. 12/144,462, Preliminary Amendment filed Jul. 7, 2008", 2 pgs.
"U.S. Appl. No. 12/144,462, Response filed Jan. 19, 2011 to Non Final Office Action mailed Oct. 19, 2010", 9 pgs.
"U.S. Appl. No. 12/144,462, Response filed Feb. 28, 2014 to Non Final Office Action mailed Nov. 29, 2013", 9 pgs.
"U.S. Appl. No. 12/144,462, Response filed May 25, 2011 to Final Office Action mailed Mar. 25, 2011", 9 pgs.
"U.S. Appl. No. 12/144,462, Response filed Jul. 25, 2011 to Final Office Action mailed Mar. 25, 2011", 9 pgs.
"U.S. Appl. No. 12/627,861, Non Final Office Action mailed Aug. 26, 2010", 6 pgs.
"U.S. Appl. No. 12/627,861, Response filed Nov. 24, 2010 to Non Final Office Action mailed Aug. 26, 2010", 3 pgs.
"Canadian Application Serial No. 2,534,119, Office Action mailed Feb. 11, 2013", 3 pgs.
"European Application Serial No. 04779473.0, Office Action mailed Feb. 9, 2007", 4 pgs.
"European Application Serial No. 04779473.0, Office Action mailed Jul. 17, 2006", 5 pgs.
"European Application Serial No. 04779473.0, Response filed Jul. 30, 2007 to Office Action mailed Feb. 9, 2007", 10 pgs.
"European Application Serial No. 04779473.0, Response filed Nov. 28, 2006 to Office Action mailed Jul. 17, 2006", 10 pgs.
"European Application Serial No. 06025668.2, Extended European Search Report mailed Mar. 14, 2007", 7 pgs.
"European Application Serial No. 06025668.2, Office Action mailed Jul. 26, 2010", 2 pgs.
"European Application Serial No. 06025668.2, Office Action mailed Nov. 8, 2007", 1 pgs.
"European Application Serial No. 06025668.2, Office Action mailed Nov. 18, 2008", 4 pgs.
"European Application Serial No. 06025668.2, Response filed Mar. 26, 2009 to Office Action mailed Nov. 18, 2008", 4 pgs.
"European Application Serial No. 06025668.2, Response filed Apr. 22, 2008 to Office Action mailed Nov. 8, 2007", 7 pgs.
"European Application Serial No. 06025668.2, Response filed Dev. 2, 2010 to Office Action mailed Jul. 26, 2010", 10 pgs.

(56) References Cited

OTHER PUBLICATIONS

"International Application Serial No. PCT/US2004/024426, International Preliminary Report on Patentability mailed Jan. 30, 2006", 7 pgs.

"International Application Serial No. PCT/US2004/024426, International Search Report mailed Feb. 21, 2005", 3 pgs.

"International Application Serial No. PCT/US2004/024426, Written Opinion mailed Feb. 21, 2005", 6 pgs.

Burri, et al., "Utility of the Surface ECG Before VDD Pacemaker Implantation", International Journal of Cardiology, vol. 117, No. 2, (Apr. 25, 2007), 211-213.

MULTIPLE ELECTRODE VECTORS FOR IMPLANTABLE CARDIAC TREATMENT DEVICES

REFERENCE TO RELATED APPLICATIONS

This application is a continuation of U.S. patent application Ser. No. 14/452,859, filed Aug. 6, 2014, titled VECTOR SWITCHING IN AN IMPLANTABLE CARDAIC STIMULUS SYSTEM, now U.S. Pat. No. 9,345,899, which is a continuation of U.S. patent application Ser. No. 12/144,462, filed Jun. 23, 2008, now U.S. Pat. No. 8,825,157, titled VECTOR SWITCHING IN AN IMPLANTABLE CARDAIC STIMULUS SYSTEM, which is a divisional of U.S. patent application Ser. No. 10/901,258, filed Jul. 27, 2004, now U.S. Pat. No. 7,392,085 and titled MULTIPLE ELECTRODE VECTORS FOR IMPLANTABLE CARDIAC TREATMENT DEVICES, which claims the benefit of U.S. Provisional Application Ser. No. 60/490,779, filed Jul. 28, 2003, and titled MULTIPLE ELECTRODE VECTORS IN A SUBCUTANEOUS ICD, the entire disclosures of which are herein incorporated by reference.

This application is related to U.S. patent application Ser. No. 11/120,284, filed May 2, 2005, titled MULTIPLE ELECTRODE VECTORS FOR IMPLANTABLE CARDIAC TREATMENT DEVICES, now U.S. Pat. No. 7,627,367, the disclosure of which is herein incorporated by reference, and which claims priority as outlined below to the following applications for which the entire disclosures of each are also herein incorporated by reference:
- a continuation of U.S. patent application Ser. No. 10/901,258, filed Jul. 27, 2004, now U.S. Pat. No. 7,392,085 and titled MULTIPLE ELECTRODE VECTORS FOR IMPLANTABLE CARDIAC TREATMENT DEVICES, which further claims the benefit of U.S. Provisional Application Ser. No. 60/490,779, filed Jul. 28, 2003;
- a continuation-in-part of U.S. patent application Ser. No. 10/856,084, filed May 27, 2004, now U.S. Pat. No. 7,330,757, and titled METHOD FOR DISCRIMINATING BETWEEN VENTRICULAR AND SUPRAVENTRICULAR ARRHYTHMIAS, which claims the benefit of U.S. Provisional Application Ser. No. 60/474,323, filed May 29, 2003;
- a continuation-in-part of U.S. patent application Ser. No. 10/863,599, filed Jun. 8, 2004, now U.S. Pat. No. 7,379,772, and titled APPARATUS AND METHOD OF ARRHYTHMIA DETECTION IN A SUBCUTANEOUS IMPLANTABLE CARDIOVERTER/DEFIBRILLATOR, which is a continuation of U.S. patent application Ser. No. 09/990,510, filed Nov. 21, 2001, now U.S. Pat. No. 6,754,528, and titled APPARATUS AND METHOD OF ARRHYTHMIA DETECTION IN A SUBCUTANEOUS IMPLANTABLE CARDIOVERTER/DEFIBRILLATOR;
- a continuation-in-part of U.S. patent application Ser. No. 10/858,598, filed Jun. 1, 2004, now U.S. Pat. No. 7,248,921, and titled METHOD AND DEVICES FOR PERFORMING CARDIAC WAVEFORM APPRAISAL, which claims the benefit of U.S. Provisional Application Ser. No. 60/475,279, filed Jun. 2, 2003.

FIELD OF THE INVENTION

The present invention relates generally to methods and devices for improving sensing in an implantable cardiac treatment system. More particularly, the present invention relates to the placement of electrodes in an implantable pacing or cardioversion/defibrillation system at defined locations within a patient to create multiple electrode vectors for improved far-field sensing and improved sensing of cardiac events.

BACKGROUND

Implantable cardiac rhythm management devices are an effective treatment in managing irregular cardiac rhythms in particular patients. Implantable cardiac rhythm management devices are capable of recognizing and treating arrhythmias with a variety of therapies. These therapies include anti-bradycardia pacing for treating bradycardia, anti-tachycardia pacing or cardioversion pulsing for treating ventricular tachycardia, and high energy shocking for treating ventricular fibrillation. Usually, the cardiac rhythm management device delivers these therapies for the treatment of tachycardia in sequence starting with anti-tachycardia pacing and then proceeding to low energy shocks, and then finally to high energy shocks. Sometimes, however, only one of these therapies is selected depending upon the tachyarrhythmia detected.

To effectively deliver treatment, cardiac rhythm management devices must first accurately detect and classify a cardiac event. Through the accurate classification of cardiac events, these cardiac rhythm management devices are able to classify the type of arrhythmia that is occurring (if any) and assess the appropriate therapy to provide to the heart (if indicated). A problem arises, however, when the cardiac rhythm management device misclassifies an event and, as a result, delivers inappropriate therapy or fails to deliver therapy.

Besides being physically painful to the patient, when a cardiac rhythm management device delivers inappropriate treatment, it can be extremely disconcerting. Moreover, delivery of an inappropriate therapy can intensify the malignancy of the cardiac arrhythmia or cause an arrhythmia where one was not present. The accuracy of a sensing architecture is, therefore, an important factor in ensuring that appropriate therapy is delivered to a patient.

SUMMARY

In a first embodiment, an implantable cardiac treatment system is provided with electrodes disposed at several locations in a patient's thorax. During operation of the system, various sensing vectors can be periodically, repeatedly, or continuously monitored to select the best sensing vector for event detection and classification. A sensing vector may be selected and then used for analysis. In another embodiment, multiple vectors may be simultaneously analyzed to provide a tiered or prioritized detection scheme, or to provide a secondary check on a higher priority vector. For example, a first vector may be used as the higher priority vector, and a second vector may be used to verify that sensed with the first vector. Alternatively, ambiguity may be reduced by the use of a second vector to check on a first vector. Additional embodiments include implantable cardiac treatment systems and operational circuitry for use in implantable cardiac treatment systems which are adapted for performing these methods. Some embodiments take the form of subcutaneous implantable cardiac treatment systems.

DETAILED DESCRIPTION

The following detailed description should be read with reference to the Figures, in which like elements in different Figures are numbered identically. The Figures, which are not necessarily to scale, depict selected embodiments and are not intended to limit the scope of the invention. Those skilled in the art will recognize that many of the examples and elements of the examples have suitable alternatives that may be utilized.

The present invention is generally related to cardiac rhythm management devices (e.g., an Implantable Cardioverter/Defibrillator (ICD) system) that provide therapy for patients experiencing particular arrhythmias. The present invention is directed toward sensing architectures for use in cardiac rhythm management devices. In particular, the present invention is suited for ICD systems capable of detecting and defibrillating harmful arrhythmias. Although the sensing architecture is intended primarily for use in an implantable medical device that provides defibrillation therapy, the invention is also applicable to cardiac rhythm management devices directed toward anti-tachyarrhythmia pacing (ATP) therapy, pacing, and other cardiac rhythm devices capable of performing a combination of therapies to treat rhythm disorders, including external devices.

Figure 1A:
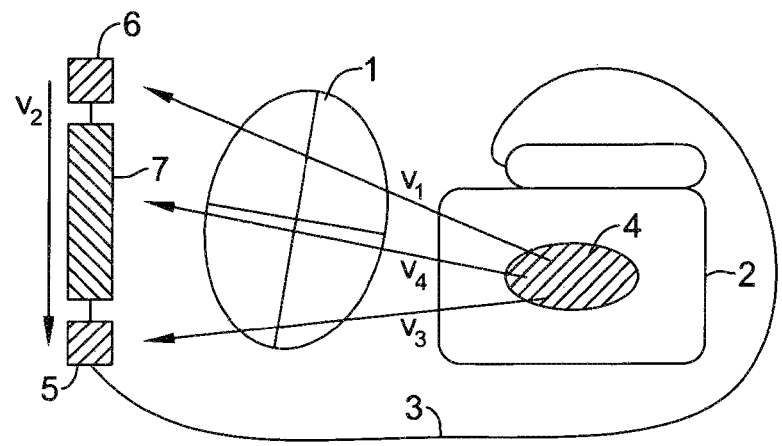
FIGS. 1A-1B illustrate, respectively, representative subcutaneous and intravenous implantable cardiac treatment systems.
Figure 1B:
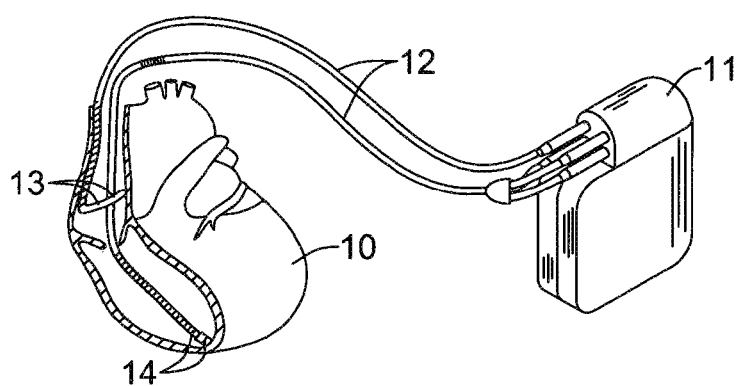

To date, ICD systems have been epicardial systems or transvenous systems implanted generally as shown in FIG. 1B, however, as further explained herein, the present invention is also adapted to function with a subcutaneous ICD system as shown in FIG. 1A.

FIG. 1A illustrates a subcutaneously placed ICD system. In this illustrative embodiment, the heart 1 is monitored using a canister 2 coupled to a lead system 3. The canister 2 may include an electrode 4 thereon, while the lead system 3 connects to sensing electrodes 5, 6, and a coil electrode 7 that may serve as a shock or stimulus delivery electrode as well as a sensing electrode. The general path between various electrodes defines a number of sensing vectors V1, V2, V3, V4. It can be seen that each vector provides a different vector "view" of electrical activity in the heart 1. The system may be implanted subcutaneously as illustrated, for example, in U.S. Pat. Nos. 6,647,292 and 6,721,597, the disclosures of which are both incorporated herein by reference. By subcutaneous placement, it is meant that sensing and therapy can be accomplished with electrode placement that does not require insertion of an electrode into a heart chamber, the heart muscle, or the patient's vasculature.

FIG. 1B illustrates a transvenous ICD system. The heart 10 is monitored and treated by a system including a canister 11 coupled to a lead system 12 including atrial electrodes 13 and ventricular electrodes 14. A number of configurations for the electrodes may be used, including placement within the heart, adherence to the heart, or disposition within the patient's vasculature. For example, Olson et al., in U.S. Pat. No. 6,731,978, illustrate electrodes disposed in each chamber of the heart for sensing, as well as shocking electrodes in addition to the sensing electrodes.

The present invention, in some embodiments, is also embodied by operational circuitry including select electrical components provided within the canister 2 (FIG. 1A) or canister 11 (FIG. 1B). In such embodiments, the operational circuitry may be configured to enable the methods to be performed. In some similar embodiments, the present invention may be embodied in readable instruction sets such as a program encoded in machine or controller readable media, wherein the readable instruction sets are provided to enable the operational circuitry to perform the analysis discussed herein in association with various embodiments. Further embodiments may include a controller or microcontroller adapted to read and execute embodiments discussed herein.

In the system illustrated in FIG. 1A, the subcutaneous implantable cardiac treatment device can sense a plurality of electrode vectors. In particular, the configuration depicted can sense at least between the first sensing electrode 6 and the canister or housing electrode 4. The canister or housing electrode 4 can be a part of the housing or canister, the housing or canister itself may be an electrode 4, or alternatively, the electrode can be attached to or on the housing. This sensing relationship forms electrode vector $v_1$. The device can further sense between the first sensing electrode 6 and the second sensing electrode 5 to form electrode vector $v_2$. A third sensing configuration is created by sensing between the second sensing electrode 5 and the canister electrode 4. This sensing relationship forms electrode vector $v_3$. The last illustrated electrode vector is between the shocking electrode 7 and the canister electrode 4 forming electrode vector $v_4$. The system depicted in FIG. 1a is illustrative only. The purpose of the Figure is to demonstrate some of the possible electrode vectors that can be formed with implantable cardioverter-defibrillator systems, particularly with subcutaneous systems. Other electrode arrangements and electrode types may be utilized without deviating from the spirit and scope of the invention.

Figure 2:
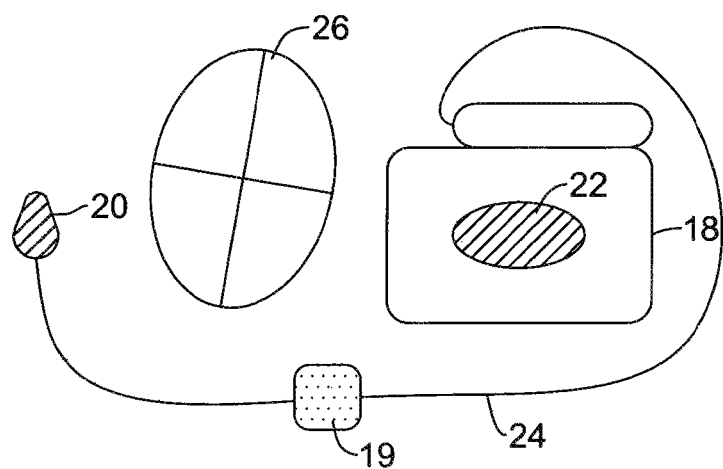
FIG. 2 shows a subcutaneous implantable cardiac treatment system having an alternative subcutaneous electrode system arrangement.

An alternative subcutaneous embodiment is depicted in FIG. 2. A canister 18 is electrically coupled to electrodes 19, 20, 22, with electrodes 19, 20 disposed on a lead 24 and electrode 22 disposed on the canister 18. The several electrodes 19, 20, 22 provide various sensing vectors around heart 26. The illustrative leads and electrodes may have various lengths. As further discussed below, certain sizes and lengths may provide advantageous sensing characteristics.

Figure 3A:
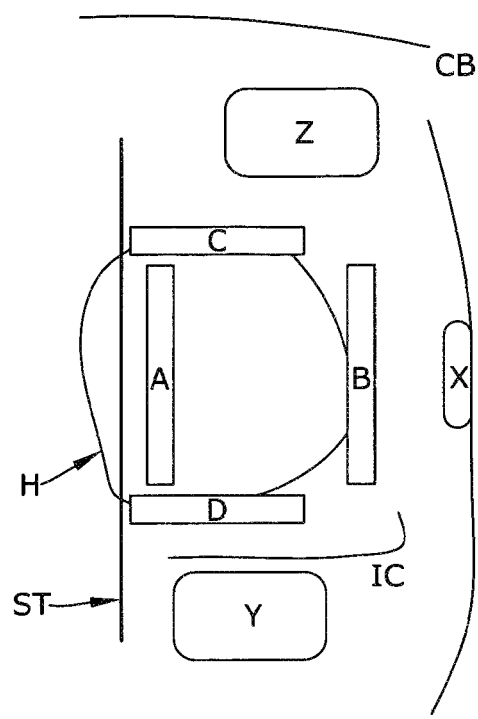
FIGS. 3A and 3B show three positions for the placement of an implantable cardiac treatment device and four subcutaneous positions for the placement of an electrode.
Figure 3B:
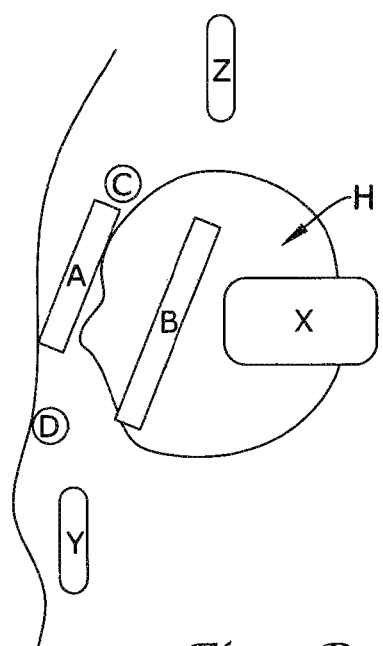

FIGS. 3A and 3B show three illustrative subcutaneous positions (X, Y and Z) for the placement of an ICD in a patient's thoracic region. FIG. 3A is a view from the front, facing a patient's chest, while FIG. 3B is a view from the left of a patient, each view showing only the ICD components and the heart. Position X is disposed on the left side of the rib cage, inferior to the arm, and is designated herein as the lateral position. Position Y is a frontal position, inferior to the inframammary crease (IC) and is designated herein as the inframammary position. Finally, position Z is also a frontal position and can correspond to a conventional positioning for ICDs. This position is located superior and to the left of the heart (H) and inferior the collarbone (CB). This position Z is designated herein as the pectoral position.

Similarly, FIGS. 3A and 3B show four subcutaneous positions (A, B, C and D) for the placement of the subcutaneous electrode system 12 upon a patient's thoracic region. Position A is a parasternal placement that is positioned on the left side of the sternum (ST). Position B is an electrode placement that runs parallel to the sternum (ST), but position B is located laterally as opposed to the parasternal placement of position A. Position C is an electrode placement that is generally orthogonal to positions A and B and is positioned on a line superior to the heart (H). Finally, position D is an electrode placement that is parallel with position C, but has the electrode positioned in a line inferior to the patient's heart (H).

Figure 4:
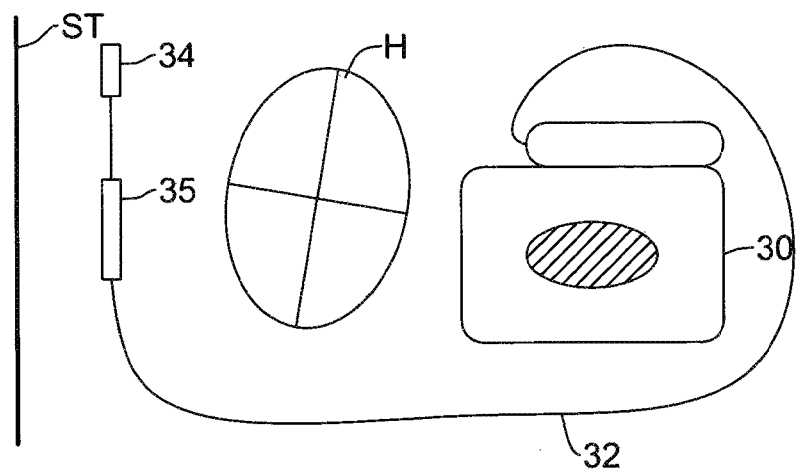
FIG. 4 illustrates a laterally placed implantable cardiac treatment system with a parasternally placed electrode.

FIG. 4 illustrates a laterally placed (X) ICD canister 30 with a parasternally placed (position A) subcutaneous electrode system along lead 32. FIG. 4 shows the lead 32 traversing subcutaneously along the ribcage and terminating in a position where the subcutaneous electrode system of the lead 32 is disposed vertically and parallel to the patient's sternum (ST). The first sensing electrode 34 is shown positioned at or near a line superior to the patient's heart (H). A coil electrode 35 is also shown, with the coil electrode 35 coupled for use as a shocking electrode, and, optionally, as an additional sensing electrode.

Figure 5:
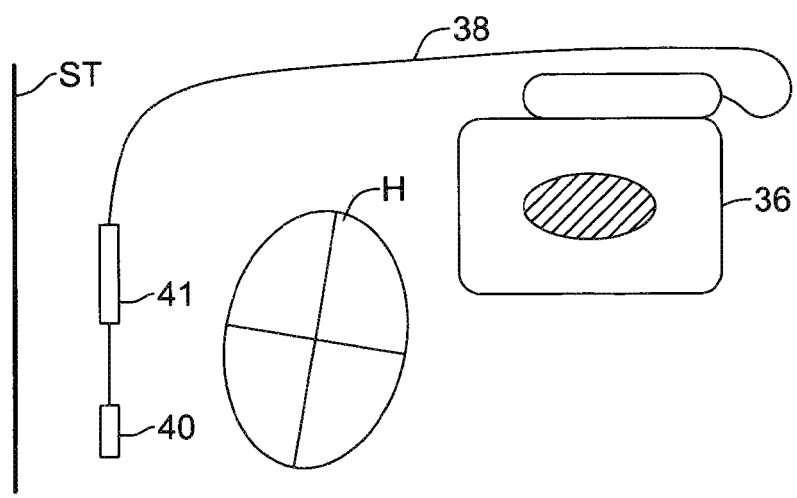
FIG. 5 illustrates a pectorally placed implantable cardiac treatment system with a parasternally placed electrode.

FIG. 5 similarly illustrates a pectorally placed (Z) ICD canister 36 with a parasternally placed (position A) subcutaneous electrode system including a lead 38. FIG. 5 also shows the lead 38 traversing subcutaneously along the ribcage and terminating such that the subcutaneous electrode system of the lead 38 is disposed vertically and parallel to the patient's sternum (ST). In contrast to the electrode placement in FIG. 3, the first sensing electrode 40 of the subcutaneous electrode system is positioned at or near a line inferior to the patient's heart (H). Again, a coil electrode 41 serving as a shocking and, if desired, sensing electrode is also illustrated.

The subcutaneous space surrounding a patient's thoracic region is inherently curvaceous. Because the canister 30, 36 (which may include a sensing electrode) and the subcutaneous electrode system on leads 32, 38 are positioned upon this region, the electrodes, canister and lead for the ICD are rarely, if ever, planar with respect to one another. Thus various vectors may be defined to intersect the heart (H), without necessarily having to place electrodes in the heart (H).

The distance separating the canister 30, 36 and the electrodes on the leads 32, 38 is dependent on the patient's anatomy. With the configurations shown in FIGS. 4 and 5, in a typical adult patient, the center of the canister 30, 36 is approximately 8 cm to approximately 19 cm away from the center of a shocking coil 35, 41 on the leads 32, 38. Children receiving devices according to the present invention may have separations between the canister and the shocking coil 35, 41 of generally no less than approximately 4 cm.

Subcutaneous embodiments of the present invention benefit from the ability to optimize the intra-electrode distance to maximize the sensing of cardiac electrical activity. Because subcutaneous embodiments of the present invention are not constrained by the location of electrodes within the system or within the patient's thorax, a subcutaneous system may use intra-electrode distances particularly chosen for optimizing far-field signal sensing, or may vary the sensing electrode pair during operation to optimize sensing.

FIG. 6A-6F depict observed electrocardiogram (EKG) signals from two small surface area electrodes having differing intra-electrode distances. In these figures, one of the two small surface area electrodes was placed in a fixed position located laterally 0.5" from the sternum, and over the patient's heart. The second of the two small surface area electrodes was positioned specific distances from the first electrode to observe and record the change in the resulting EKG.

Figure 6A:
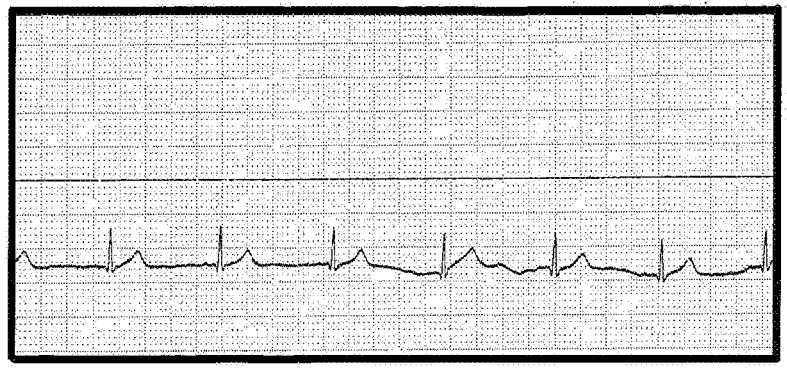
FIGS. 6A-6F depict recorded electrocardiograms from several discrete intra-electrode distances.
Figure 6B:
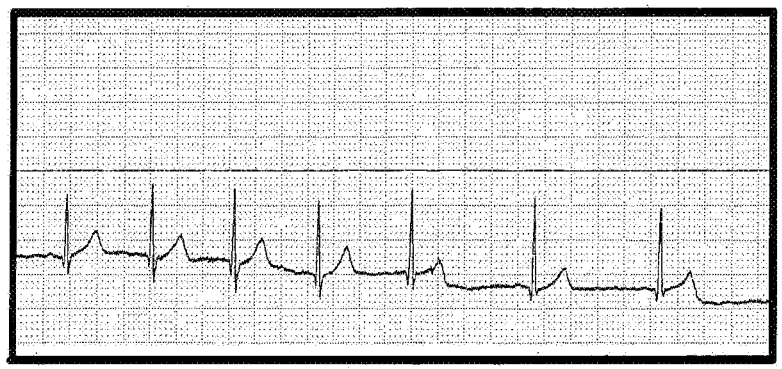
Figure 6C:
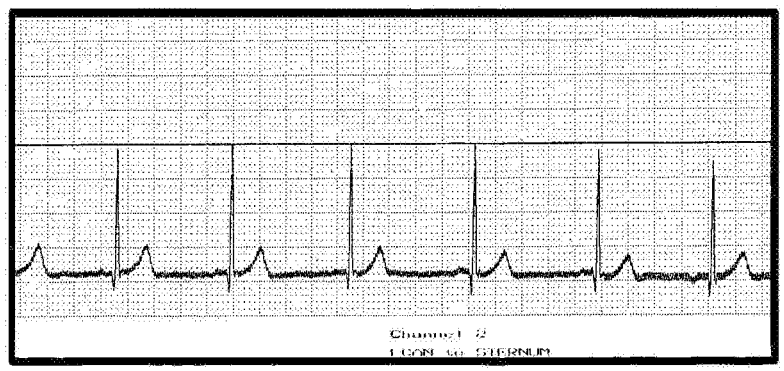
Figure 6D:
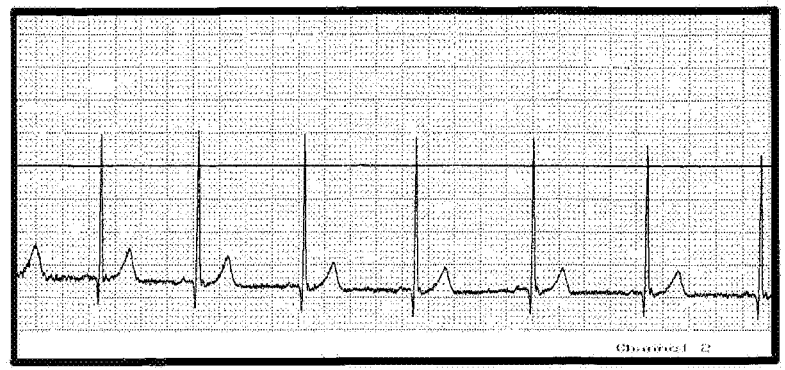
Figure 6E:
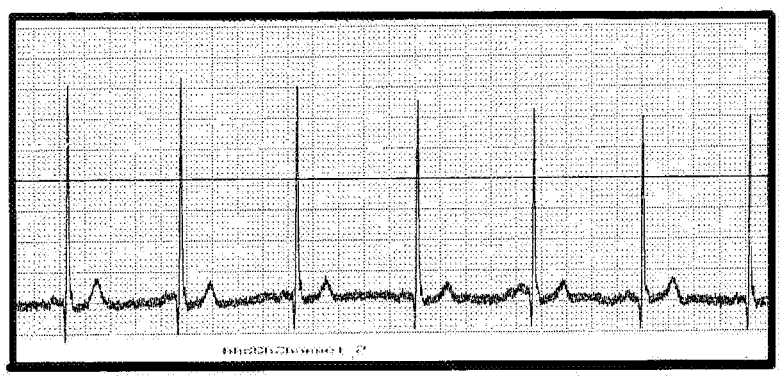
Figure 6F:

Initially, the second electrode was placed laterally 0.75" from the fixed electrode, thereby creating an intra-electrode distance of approximately 0.75". An EKG was then observed of the cardiac electrical activity. FIG. 6A represents a portion of the recorded EKG where the electrodes possessed an intra-electrode distance of approximately 0.75". Additional EKGs were recorded to measure the sensed cardiac activity after positioning the second electrode laterally approximately 1.25", 2", 2.5", 3.25" and 5.5" away from the fixed electrode position. The resulting EKGs are shown in FIGS. 6B-6F, respectively. The average observed amplitude for the QRS complex was approximately 1.0 mV in FIG. 6A, approximately 2.0 mV in FIG. 6B, approximately 4.4 mV for FIG. 6C, approximately 5.5 mV for FIG. 6D, approximately 7.8 mV for FIG. 6E and approximately 9.6 mV for FIG. 6F.

Subcutaneous embodiments of the present invention are not constrained by the location of electrodes to intravenous or intracardiac locations. As such, the subcutaneous system may use intra-electrode distances that are particularly chosen for optimizing far-field signal sensing. It is observed in FIGS. 6A-6F that increasing the intra-electrode distance results in significantly increased signal amplitudes. A 100% increase in amplitude was observed between the recorded cardiac electrical activity in FIG. 6B and FIG. 6A. A 340% increase in amplitude was observed between the recorded cardiac electrical activity in FIG. 6C and FIG. 6A. A 450% increase in amplitude was observed between the recorded cardiac electrical activity in FIG. 6D and FIG. 6A. A 680% increase in amplitude was observed between the recorded cardiac electrical activity in FIG. 6E and FIG. 6A. Finally, an 860% increase in amplitude was observed between the recorded cardiac electrical activity in FIG. 6F and FIG. 6A.

It is appreciated by those skilled in the art that it is desirable to obtain the highest signal amplitudes possible when sensing. Specifically, because detected cardiac electrical signals are processed to classify particular rhythms, the larger the cardiac electrical signal the greater the opportunity to correctly classify a rhythm. Some embodiments of the present invention provide an enhanced opportunity to correctly classify arrhythmias by using intra-electrode distances particularly chosen for optimizing far-field signal sensing.

Some embodiments of the present invention are further capable of choosing the most appropriate electrode vector to sense within a particular patient. In one embodiment, (referring to FIG. 1) after implantation, the ICD is programmed to sense between several available electrode vectors—$v_1$, $v_2$, $v_3$ and $v_4$. The ICD system then senses a series of cardiac signals using some or all of the available electrode vectors, or a preset number of available electrode vectors. In certain embodiments, the ICD system then determines the most appropriate electrode vector for continuous sensing based on which electrode vector results in the greatest signal amplitude, or performs best using some other metric such as signal-to-noise ratio (SNR). The electrode vector possessing the highest quality metric (e.g., amplitude or SNR) is then set as the default electrode vector for continuous sensing. In certain embodiments, the next alternative electrode vector is selected based on being generally orthogonal to the default electrode vector. For example, if electrode vector $v_3$, is selected as the default vector, the next alternative electrode vector may be $v_2$, an electrode vector generally orthogonal to $v_3$. In yet other embodiments the next alternative electrode vector is selected based on possessing the next highest quality metric after the default electrode vector.

Recognizing that patient anatomies vary, the present invention is not intended to be limited to purely or strictly orthogonal sensing vectors. In some embodiments, generally orthogonal sensing vectors are considered to exist when two sensing vectors create an angle such that the magnitude of the cosine of the angle is less than about 0.7. In another embodiment, the magnitude of the cosine of the angle is less than about 0.5. In a further embodiment, the magnitude of the cosine of the angle is less than about 0.3. As used herein, the phrase "the magnitude of" indicates absolute value when applied to a scalar value such as the cosine of an angle. This angular analysis is used herein because, while two vectors may define a plane, an intersection of two vectors can define a plurality of angles. Analysis in terms of cosines assures the same result regardless how the vectors are disposed with respect to one another for the purpose of determining the angles therebetween. Dealing only in first quadrant angles, the above noted values for cosines yield angles of between about 45 and 90 degrees, about 60 and 90 degrees, and about 72 and 90 degrees.

In one embodiment of the present invention, the ICD system determines the most appropriate electrode vector based on results of an operation performed on all of the sensed signals. The ICD system independently operates on all of the sensed signals received from each of the possible electrode vectors using the ICD system's detection architecture. For example, the ICD system may run all of the signals from each of the electrode vectors through a correlation waveform analysis, or a similar operation function. Specifically, the ICD system performs a correlation waveform analysis on electrode vectors $v_1$, $v_2$, $v_3$ and $v_4$ independently. The ICD system then evaluates the results from each of the independently operated-on signals. This evaluation procedure determines the electrode vectors that yield the highest quality metric for rendering a decision. Finally, the ICD system selects the electrode vector yielding the highest quality metric as the default electrode vector for continuous sensing. For example, the ICD system will select the electrode vector $v_3$ as the default electrode vector if it yields the highest quality metric from the four electrode vectors evaluated.

In certain embodiments, the ICD system paretos (prioritizing according to the hierarchy of performance) the electrode vectors. By paretoing the electrode vectors, the ICD system may utilize alternative electrode vectors, in particular the next best performing electrode vectors, when ambiguities arise in analysis of the default electrode vector.

For certain embodiments of the present invention, the evaluation of the best electrode vectors for sensing are updated periodically by the physician. A programmer responsive to the ICD system may receive transmissions from the ICD system. Amongst others, the transmissions from the programmer characterize the cardiac activity sensed by each electrode vector. The physician may then select the optimal electrode vector for the particular patient and set that chosen electrode vector as the default. The programmer may additionally enable the physician to elect alternative schemes for instances where the signal from the default electrode vector is compromised. Additionally, the programmer may select the optimal electrode vector and elect alternative schemes automatically based on the received transmissions from the ICD system.

In yet alternative embodiments, the evaluation of the best electrode vectors for sensing is updated periodically by the ICD system, whether that decision is made a priori (e.g., by signal amplitude) or ex post facto (e.g., after operating on the unprocessed signal data). For example, initially the highest quality metric (e.g., highest amplitude signal) is sensed using electrode vector $v_1$. Sometime after implantation, however, the ICD system may determine that the highest quality metric is experienced when sensing through the electrode vector $v_2$. Conversely, it may be periodically determined that the best electrode vector continues to remain with electrode vector $v_1$ during the entire life of the device.

An example of an a priori update would be one where the SNR is measured for each of several vectors over time. If a muscle artifact develops after implantation, or if a fibroid forms around one of the sensing electrodes, then the relative SNR of the several sensing vectors may change over time. If one of the sensing vectors provides a superior SNR to that of the initially chosen vector, then the later update may select a different vector.

An example of an ex post facto update would be one where a particular sensing vector is chosen for a period of time, but proves to be unsuitable for analysis, for example, due to noise artifacts. For example, if a beat validation scheme is used as explained in co-pending U.S. Pat. No. 7,248,921, titled METHOD AND DEVICES FOR PERFORMING CARDIAC WAVEFORM APPRAISAL, the disclosure of which is incorporated herein by reference, then consistent failure to capture validated beats may indicate that the chosen vector is unsuitable. Likewise, if a template formation system relies upon captured data, then a failure to capture a template meeting chosen validity criteria may indicate that the chosen vector is unsuitable. In such cases, another sensing vector may be chosen by looking at the next best sensing vector. For example, if a first vector is chosen for sensing because it has a best amplitude of sensed vectors, supposing that first vector proves to be unsuitable for template formation, then a second vector having the second best amplitude may be chosen.

The periodicity used to evaluate the best electrode vector is preferably based on whether the sensed cardiac electrical signal is ambiguous to the ICD system's detection architecture. With respect to this invention, ambiguity concerns whether the sensed cardiac electrical signal is difficult to comprehend, understand, or classify by the ICD system's detection architecture. This process is illustrated by example in FIG. 7.

Figure 7:
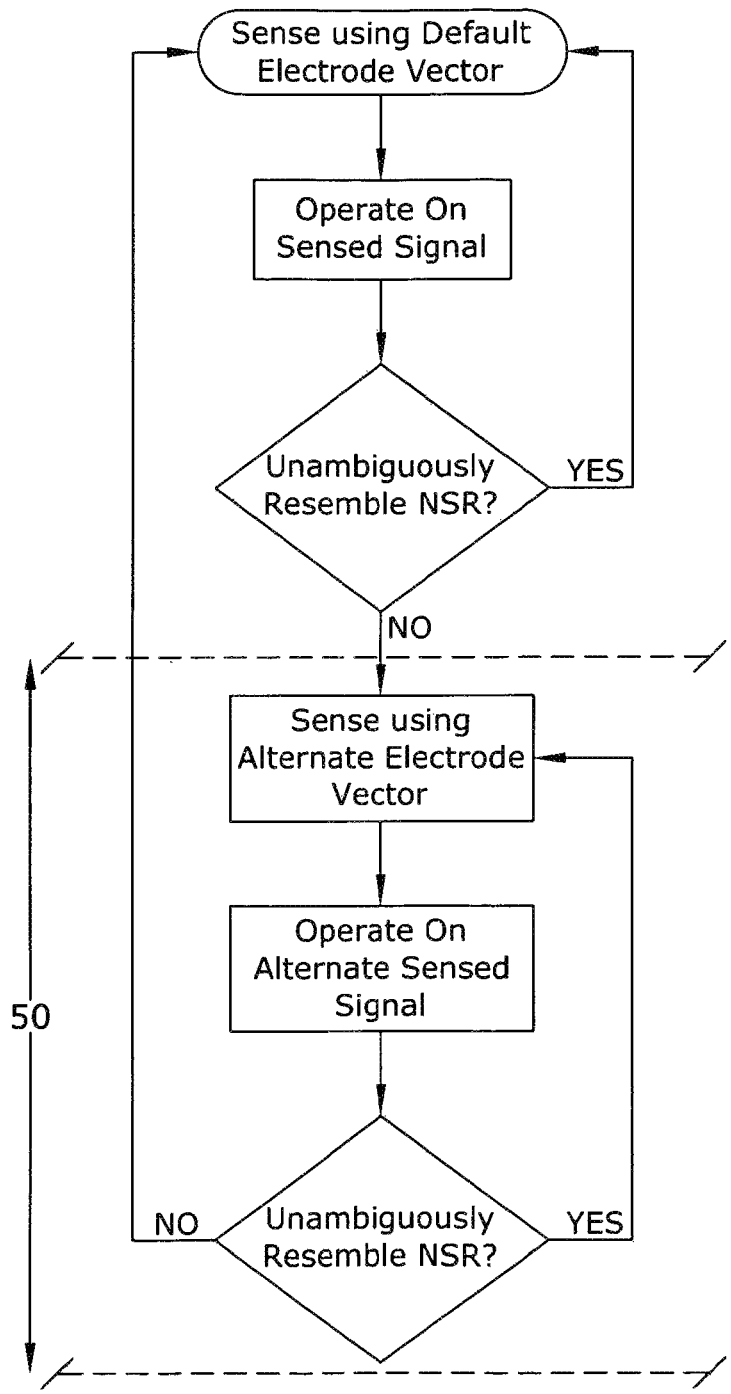
FIG. 7 shows a block diagram of the vector sensing evaluation for determining the periodicity to evaluate the best electrode vector based on observed ambiguous signals.

Referring now to FIG. 7, a cardiac electrical signal is sensed through electrode vector $v_1$. The sensed signal is then operated on by the detection architecture of the ICD system. The result of this operation is then evaluated. In certain embodiments, the ICD system will evaluate whether the operated-on signal equates unambiguously to a normal sinus rhythm. If the result of the operation unambiguously indicates a normal sinus rhythm, then the ICD system repeats the procedure and senses another cardiac electrical signal to operate upon. However, if the result of the operation is ambiguous, or the operated-on signal indicates a rhythm other than normal sinus, then the process enters a second stage 50. Some illustrative explanations of ambiguity can be found in U.S. Pat. No. 7,330,757, titled METHOD FOR DISCRIMINATING BETWEEN VENTRICULAR AND SUPRAVENTRICULAR ARRHYTHMIAS, the disclosure of which is incorporated herein by reference.

In the second stage 50, the sensing of the next cardiac electrical signal in time is performed through an alternative electrode vector. In some embodiments, the alternative electrode vector used for this sensing is one that is generally orthogonal to the electrode vector used to sense the previous signal. For example, if the previous cardiac electrical signal was sensed through electrode vector $v_1$, the next cardiac electrical signal would be sensed through electrode vector $v_2$. In alternative embodiments of the present invention, any of the remaining electrode vectors may be used to sense the next cardiac electrical signal in the second stage 50. For example, a next highest amplitude sensing vector may be chosen.

This subsequently sensed signal is then operated on by the detection architecture of the ICD system. The result of this operation is again evaluated. If the result of the operation unambiguously indicates a normal sinus rhythm from this alternative electrode vector, then the ICD system repeats the procedure and senses another cardiac signal to operate upon. In certain embodiments, subsequently sensed cardiac signals following the second stage 50 continue to be sensed through the electrode vector used for evaluation in the second stage 50. Thus in the previous example, all subsequently sensed cardiac electrical signals would be sensed using electrode vector $v_2$. However, in particular embodiments, this is only true if the result of the second stage 50 operation unambiguously indicates a normal sinus rhythm. If the result of the second stage 50 is again ambiguous, or the operated-on signal unambiguously indicates a rhythm other than normal sinus, then future sensed cardiac electrical signals may once again be processed using the default electrode vector—here being $v_1$.

In yet alternative embodiments, the next cardiac electrical signal following any second stage 50 evaluation is again initially sensed through the default electrode vector—for this example $v_1$. In this embodiment, the default electrode vector is changed only after a series of unambiguous evaluations utilizing the second stage 50 and its alternative electrode vector.

The ICD device of the present invention may also sense between multiple electrode vectors continuously and/or independently of one another. This ability allows the present invention to evaluate the same cardiac electrical signal in time from numerous vector viewpoints. Additionally, this ability permits the ICD system to evaluate the best electrode vector based on observed ambiguous signals without failing to operate and evaluate each sensed cardiac signal. Specifically, a cardiac electrical signal is sensed through an electrode vector, for example, $v_1$. The sensed signal is then operated on by the detection architecture of the ICD system. The result of this operation is then evaluated. If the result of the operation is ambiguous, or the operated-on signal unambiguously indicates a rhythm other than normal sinus, then the process enters a second stage 50.

In the second stage 50 of this embodiment, a cardiac electrical signal sensed at the same time as the sample already evaluated, but with different electrodes, is evaluated. Therefore, both the signal previously operated on and the one which is to be operated on in the second stage 50 occurred at the same time—although acquired through a different electrode vector. The sensed signal from $v_2$ is then operated on by the detection architecture of the ICD system. The result of this operation is again evaluated. If the result of the operation unambiguously indicates a normal sinus rhythm in this second electrode vector, then the ICD system repeats the procedure and senses another cardiac electrical signal in which to operate upon.

The general ability to sense between multiple sensing vectors particularly enhances specificity for detection architectures that discriminate between arrhythmias. Specifically, sensing between multiple electrode vectors enhances specificity in discriminating the origin and type of arrhythmia. In one example of the present invention, a cardiac complex representative of normal sinus rhythm (NSR) is captured from each of electrode vector $v_1$ and electrode vector $v_2$, and then stored. These are stored as NSR template 1 and NSR template 2, respectively. Because electrode vectors $v_1$ and $v_2$ are at different angles to the heart, their respective templates may differ significantly even though they may be based upon the same cardiac events.

From beat to beat, sensed complexes may be compared to their respective NSR templates. As an example, in certain vector orientations ventricular originating arrhythmias may resemble an NSR. With ICD systems that sense only one electrode vector, some ventricular arrhythmias may not be distinguishable to a detection architecture. In the present invention, however, the chances of failing to classify a particular rhythm are reduced through the use of multiple views. In particular, although a ventricular originating arrhythmia may resemble the NSR template in one view, it would be highly unlikely that a second electrode vector would also sense the same complex as resembling its NSR template.

Ventricular originating arrhythmias often exhibit a polarity flip with relation to their NSR. If this polarity flip goes undetected because of positioning in one electrode vector, a generally orthogonally positioned second electrode vector would most likely sense such a flip when compared to its NSR template. Thus, the detection algorithm would classify the uncharacteristic complex, or series of complexes, and assess the complexes as a ventricular arrhythmia.

In one embodiment, an initial analysis of the default electrode vector captured using a default electrode pair may yield an ambiguous result. For example, if a correlation waveform analysis is performed to compare a sensed signal to an NSR template, the waveform analysis may indicate that NSR is not occurring. However, it may not be clear from the initial analysis what type of arrhythmia is occurring (for example, a supraventricular arrhythmia which does not require treatment, or a ventricular arrhythmia that does require treatment). In the illustrative example, a second level of analysis may be performed using a signal captured using different electrodes to differentiate treatable and untreatable arrhythmias. The method may then return to observing only the default electrode pair.

Figure 8A:
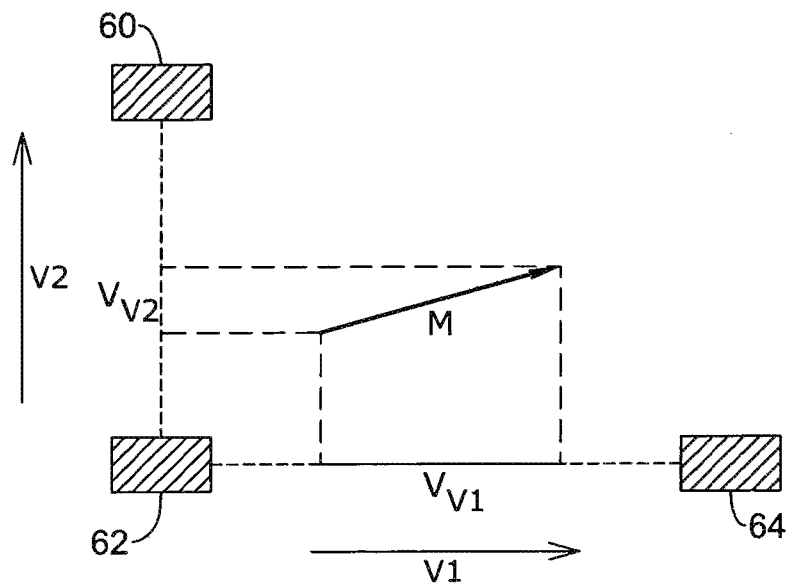
FIGS. 8A and 8B show the relationships between two electrode vectors on sensing a cardiac depolarization vector.
Figure 8B:
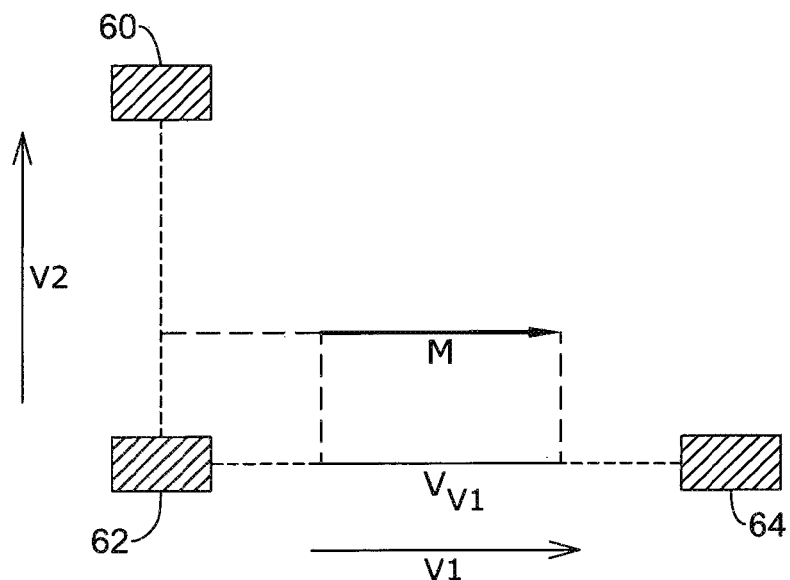

FIGS. 8A and 8B demonstrate the relationship between two electrode vectors in sensing a cardiac depolarization vector. More specifically, FIGS. 8A and 8B graphically illustrate the electrode vectors formed in the ICD system between the active canister 64 and the first sensing ring 62, and the first sensing ring 62 and the second sensing ring 60. These vectors are labeled, respectively, $v_1$ and $v_2$. FIGS. 8A and 8B further illustrate a cardiac depolarization vector M. The cardiac depolarization vector M cannot be completely described by measuring only one of the two electrode vectors shown in FIGS. 8A and 8B. More information about the cardiac depolarization vector M can be acquired using two electrode vectors. Thus, the resulting ECG derived from three or more electrodes will more accurately define a depolarization vector M, or a fraction thereof.

For the cardiac depolarization vector M, the voltage induced in the direction of electrode vector $v_1$ is given by the component of M in the direction of $v_1$. In vector algebra, this can be denoted by the dot product $$v_{v1} = M \cdot v_1$$

where $v_{v1}$ is the scalar voltage measured in the direction of electrode vector $v_1$. FIGS. 8A and 8B further depict an electrode vector $v_2$ oriented in space. The effect of the cardiac depolarization vector M as it relates to electrode vector $v_2$ differs, however, between FIGS. 8A and 8B.

FIG. 8A illustrates a cardiac depolarization vector M that includes components in both vector directions, and so is sensed and measured with scalar voltages along both electrode vectors. The cardiac depolarization vector M in FIG. 8A is oriented in space such that both electrode vectors $v_1$ and $v_2$ sense scalar voltages $v_{v1}$ and $v_{v2}$, respectively. Although the scalar voltage $v_{v1}$ predominates, the scalar voltage $v_{v2}$ is sensed and can be used for discriminating differences in the magnitude and the direction of the cardiac depolarization vector M.

In contrast, the electrode vector $v_2$ in FIG. 8B is oriented orthogonally to the cardiac depolarization vector M. In this embodiment, the component of M along the direction of vector electrode $v_2$ is zero because the $v_2$ electrode vector senses no voltage as a result of the cardiac depolarization vector; no voltage is induced in the direction of $v_2$. In contrast, the scalar voltage along $v_1$ parallels the depolarization vector M and fully captures M.

With the ability to ascertain the cardiac depolarization vector M, FIGS. 8A and 8B further depict how the present invention may be utilized to enhance a particular attribute of the sensed signal. For example, the present invention may be utilized to enhance the signal-to-noise ratio (SNR) for an ICD system. In illustration, suppose that most patients demonstrate a cardiac depolarization vector M similar to that depicted in FIG. 8A. For these patients, sensing along electrode vector $v_1$ alone would result in a sufficiently high SNR to sense and detect most arrhythmias, while vector $v_2$ provides information that may be relevant for sensing if analysis of $v_1$ contains some ambiguity.

There may be patients, however, who exhibit a cardiac depolarization vector M similar to the one depicted in FIG. 8B. These patients could exhibit a cardiac depolarization vector M at the time of implant, or after developing a pathology that changes the cardiac depolarization vector M over time to represent the one depicted in FIG. 8B. For these patients, sensing along electrode vector $v_2$ alone would result in an extremely low SNR. Furthermore, the ICD system may not be able to detect certain arrhythmic events if this were the only sensing vector the ICD system possessed. However, knowledge that $v_2$ has such a low magnitude indicates greater directional information than just analyzing $v_1$.

As described above, sensing sensitivity depends on the orientation of the cardiac depolarization vector M with respect to the orientation of the sensing electrodes.

As noted above, correlation techniques involving template comparisons may be used in the signal analysis of some embodiments of the present invention. Such analysis may be used to discriminate certain arrhythmias and direct appropriate therapy. For example, arrhythmias that indicate treatment include monomorphic ventricular tachycardia (MVT), polymorphic ventricular tachycardia (PVT) and ventricular fibrillation (VF). These are arrhythmias that are considered malignant and therefore require therapy from an implantable device such as an ICD. In contrast, certain supraventricular arrhythmias do not indicate treatment. For example, some supraventricular arrhythmias that may not indicate treatment include atrial fibrillation (AF), atrial tachycardia (AT) and sinus tachycardia (ST).

Referring now to Table 1, a comparison chart is depicted representing several comparison methods (outlined in detail below) and the predicted outcomes of these comparisons with various arrhythmias. Several of the methods make use of correlation waveform analysis (CWA). The arrhythmias in Table 1 include both ventricular arrhythmias requiring therapy and supraventricular arrhythmias where therapy should be withheld. Although Table 1 describes several comparison methods to aid in discriminating between arrhythmias, the present invention is not limited in terms of the scope of Table 1. Other comparison methods may be used, and are contemplated, to populate a similar table for discriminating between arrhythmias.

TABLE 1

|   | AF | AT/ST | MVT | PVT | VF |
|---|---|---|---|---|---|
| A | HIGH | HIGH | LOW | LOW | LOW |
| B | LOW | LOW | LOW | HIGH | HIGH |
| C | HIGH | HIGH | HIGH | LOW | LOW |
| D | LOW | LOW | LOW | HIGH | HIGH |
| E | NARROW | NARROW | WIDE | WIDE | WIDE |
| F | LOW | HIGH | HIGH | LOW | LOW |
| G | NO | YES/NO | YES | YES | YES |

Table 1 uses the following comparison methods and their corresponding definitions:

A=CWA between a sensed complex and a stored sinus template, where HIGH indicates high correlation with a stored sinus template and LOW indicates low correlation with a stored sinus template;

B=Variability in the CWA between a sensed complex and a stored sinus template, where HIGH indicates high variability within a grouping of cardiac complexes and LOW indicates low variability within a grouping of cardiac complexes;

C=CWA between a sensed complex and a template acquired after a triggering event (here, a template representative of a complex with a rate between 170 and 260 bpm), where HIGH indicates high correlation with the template acquired after a triggering event and LOW indicates low correlation with the template acquired after a triggering event;

D=Variability in the CWA between a sensed complex and a template acquired after a triggering event (here, a template representative of a complex with a rate between 170 and 260 bpm), wherein the template is dynamic and continually updated by the previously sensed cardiac complex, where HIGH indicates high variability in the CWA, within a grouping of cardiac complexes when compared to a template acquired after a triggering event and LOW indicates low variability in the CWA within a grouping of cardiac complexes when compared to a template acquired after a triggering event;

E=Comparison to a QRS width threshold value (described in detail above), where WIDE indicates QRS waveforms having greater that 35 percent of their complex laying above the width threshold value and NARROW indicates QRS waveforms having less that 35 percent of their complex laying above the width threshold value;

F=Interval rate stability of +/−30 milliseconds, where YES indicates stability within +/−30 milliseconds and NO indicates stability outside of +/−30 milliseconds; and G=A rate acceleration event, where YES indicates a rate accelerating event and NO indicates the lack of a rate accelerating event.

Thresholds indicating whether a CWA score is "high" or "low" may be set in any suitable manner. Some examples of such analysis are shown in U.S. Pat. No. 7,330,757, titled METHOD FOR DISCRIMINATING BETWEEN VENTRICULAR AND SUPRAVENTRICULAR ARRHYTHMIAS.

Certain arrhythmias in Table 1 are strongly indicated when processed through certain comparison methods. These results are unambiguous even when sensed by transvenous lead systems. An example of this phenomenon is the strong indications observed in PVT and VF arrhythmias when running comparison method A. Specifically, a sensed PVT or VF arrhythmic complex will almost always correlate poorly (score as LOW) when compared to a stored sinus template. The ambiguity in this comparison is extremely low with these arrhythmias. Thus, scoring a LOW in comparison method A lends itself to a strong indication for these two particular arrhythmias.

Table 2 shows which of the illustrative comparison methods tease out particular arrhythmias with little to no ambiguity, or alternatively, show a strong indication for the particular arrhythmia.

TABLE 2

|   | AF | AT/ST | MVT | PVT | VF |
|---|----|-------|-----|-----|-----|
| A | — | — | — | LOW | LOW |
| B | — | LOW | LOW | HIGH | HIGH |
| C | — | — | — | LOW | LOW |
| D | — | LOW | LOW | HIGH | HIGH |
| E | — | — | — | — | — |
| F | — | — | — | LOW | LOW |
| G | — | —/NO | — | — | — |

Certain entries in Table 1 are influenced by some ambiguity. Because Table 1 was tabulated from data observed by transvenous lead systems, these systems cannot always unambiguously discern vector information that distinguishes attributes specific to particular arrhythmias. The reason for this is that transvenous electrode systems are optimized for local information sensing, and this optimization comes at the expense of far field and vector information sensing. This relative lack of far field and vector information sensing translates to relatively frequent ambiguous sensing with certain arrhythmias, such as an atrial fibrillation that conducts rapidly to the ventricles.

The ambiguity of certain arrhythmias can be high in particular comparison methods. Table 3 shows which of the illustrative comparison methods tease out particular arrhythmias with high ambiguity and their corresponding estimate of ambiguity percentage for a transvenous approach. Table 3 shows the weak indicators for particular arrhythmias. Again, this ambiguity is primarily the result of the data propagating Tables 1-3 being observed from transvenous lead systems.

TABLE 3

|   | AF | AT/ST | MVT | PVT | VF |
|---|----|-------|-----|-----|-----|
| A | — | — | LOW (20%) | — | — |
| B | — | — | — | — | — |
| C | — | — | HIGH (20%) | — | — |
| D | — | — | — | — | — |

TABLE 3-continued

|   | AF | AT/ST | MVT | PVT | VF |
|---|----|-------|-----|-----|-----|
| E | NARROW (33%) | NARROW (33%) | — | — | — |
| F | — | — | — | — | — |
| G | NO (20%) | — | — | YES (20%) | YES (20%) |

Of note, the ambiguity percentages used in Table 3, and all subsequent Tables, are educated estimations based on published studies and clinical observations. It is believed that these results are suitable for extrapolation to a larger population. However, ambiguities in the Tables exist. For example, it is estimated that about 20% of the population will contraindicate an MVT when using either comparison method A or comparison method C. For some embodiments of the present invention, these ambiguity percentages provide a tool for planning a multi-comparison methodology. By knowing the relative ambiguities of any particular comparison method, the detection enhancement operator may determine particular comparison methods more efficaciously over others when discerning particular arrhythmias.

An example of the ambiguity of certain arrhythmias when using certain comparison methods is illustrated when examining comparison method A. In illustration, in transvenous studies, although a MVT arrhythmia will generally correlate poorly (score as LOW) when compared to a stored sinus template, there is an approximately 20 percent chance that a MVT may demonstrate a high correlation and actually score HIGH using the same comparison method. Thus, the influence of these more ambiguous results is troubling when discriminating between arrhythmias, and ultimately in directing therapy. Layered analysis may aid in reducing the ambiguity. For example, layers having more than one method of analyzing data from a single sensing view, and layers analyzing data from more than one sensing view, may aid in reducing ambiguities.

The operational circuitry used in the implantable medical devices of the present invention may be configured to include such controllers, microcontrollers, logic devices, memory, and the like, as selected, needed, or desired for performing the steps for which each is configured.

In addition to uses in an ICD system, the present invention is also applicable to pacing systems. For example, in a pacing system a number of electrodes may be disposed to define several sensing vectors, and the present invention may guide the selection of and periodic updating of sensing vectors.

In one illustrative example, the present invention is embodied in an implantable cardiac treatment system comprising an implantable canister housing operational circuitry and a plurality of electrodes electrically coupled to the operational circuitry wherein the operational circuitry is configured and coupled to the electrodes to define at least a first implanted electrode pair and a second implanted electrode pair. The operational circuitry may be configured to perform the steps of capturing a first signal from the first implanted electrode pair, constructing a first template using the first signal, capturing a second signal from the second implanted electrode pair, constructing a second template using the second signal, and capturing a signal using the first and second electrode pairs and using the first and second templates to determine whether a treatable cardiac condition exists.

Numerous characteristics and advantages of the invention covered by this document have been set forth in the foregoing description. It will be understood, however, that this disclosure is, in many aspects, only illustrative. Changes may be made in details, particularly in matters of shape, size and arrangement of parts without exceeding the scope of the invention. The invention's scope is defined, of course, in the language in which the claims are expressed.

What is claimed is:

1. An implantable medical device comprising operational circuitry configured to receive cardiac electrical signals from at least first, second and third implantable electrodes such that at least first and second sensing vectors for sensing cardiac electrical signals are available to the operational circuitry, wherein the operational circuitry is configured to analyze cardiac activity in order to identify an arrhythmia as follows:
   receiving signals from each of the first and second sensing vectors including capturing a representation of a cardiac signal in each of the first and second vectors;
   analyzing the representation of the cardiac signal captured from the first sensing vector to generate a first result;
   determining whether the first result unambiguously indicates a non-malignant cardiac rhythm and:
      if the first result does not unambiguously indicate a non-malignant cardiac rhythm, analyzing the representation of the cardiac signal captured using the second vector;
      if the first result unambiguously indicates a non-malignant cardiac rhythm, foregoing analysis of the representation of the cardiac signal captured using the second vector.

2. The device of claim 1 wherein the operational circuitry is configured such that the first result is generated from a measure of variability of correlation between representations of the cardiac signal captured from the first vector and a stored template.

3. The device of claim 2 wherein the operational circuitry is configured such that the non-malignant cardiac rhythm is one of atrial tachycardia or sinus tachycardia.

4. The device of claim 1 wherein the operational circuitry is configured such that the first result is generated from a measure of variability of correlation between representations of the cardiac captured from the first vector and a template acquired after a triggering event.

5. The device of claim 4 wherein the operational circuitry is configured such that the triggering event is the identification of a rate between 170 and 260 beats per minute.

6. The device of claim 4 wherein the operational circuitry is configured such that the non-malignant cardiac rhythm is one of atrial tachycardia or sinus tachycardia.

7. The device of claim 1 wherein the operational circuitry is configured such that the first result is generated from observation that no rate acceleration event has taken place, and wherein the non-malignant cardiac rhythm is sinus tachycardia.

8. The device of claim 1 wherein the operational circuitry is housed in a canister along with a battery and high voltage circuitry for delivery of electrical defibrillation or cardioversion therapy, the canister being adapted to receive a lead having a plurality of electrodes thereon, such that the first, second and third electrodes comprise at least one electrode on the canister and at least one electrode on a lead.

9. The device of claim 8 wherein the operational circuitry is configured to deliver defibrillation therapy in response to identification of a malignant arrhythmia, and to withhold defibrillation therapy if a non-malignant cardiac rhythm is identified.

10. An implantable medical device system comprising the device of claim 8 and an implantable lead having a plurality of electrodes thereon.

11. An implantable medical device comprising operational circuitry configured to receive cardiac electrical signals from at least first, second and third implantable electrodes such that at least first and second sensing vectors for sensing cardiac electrical signals are available to the operational circuitry, wherein the operational circuitry is configured to analyze cardiac activity in order to identify an arrhythmia as follows:
   receiving signals from each of the first and second sensing vectors including capturing a representation of a cardiac signal in each of the first and second vectors;
   analyzing the representation of the cardiac signal captured from the first sensing vector to generate a first result;
   determining whether the first result unambiguously indicates the presence of a malignant arrhythmia and:
      if the first result does not unambiguously indicate the presence of a malignant cardiac rhythm, analyzing the representation of the cardiac signal captured using the second vector;
      if the first result unambiguously indicates the presence of a malignant cardiac rhythm, foregoing analysis of the representation of the cardiac signal captured using the second vector and concluding that the cardiac signal captured by the representation in each of the first and second vectors indicates an arrhythmia.

12. The implantable medical device of claim 11 wherein the operational circuitry is configured such that the first result is generated by comparing the representation of the cardiac signal captured from the first sensing vector to a stored template of sinus rhythm, and if the first result indicates low correlation it is found to unambiguously indicate the presence of a malignant cardiac rhythm that is one of polymorphic ventricular tachycardia, or ventricular fibrillation.

13. The implantable medical device of claim 11 wherein the operational circuitry is configured such that the first result is generated from a measure of variability of correlation between sensed representations along the first vector and a stored template, and if the first result indicates low variability it is found to unambiguously indicate the presence of a malignant cardiac rhythm that is monomorphic ventricular tachycardia.

14. The implantable medical device of claim 11 wherein the operational circuitry is configured such that the first result is generated by comparing the representation of the cardiac signal captured from the first sensing vector to a template of cardiac signal captured after a triggering event in which the rate is in the range of 180 to 260 beats per minute, and if the first result indicates low correlation it is found to unambiguously indicate the presence of a malignant cardiac rhythm that is one of polymorphic ventricular tachycardia, or ventricular fibrillation.

15. The implantable medical device of claim 11 wherein the operational circuitry is configured such that the first result is generated from a measure of variability of correlation between representations of the cardiac signal from first vector and a template of cardiac signal captured after a triggering event in which the rate is in the range of 180 to 260 beats per minute, and if the first result indicates low variability it is found to unambiguously indicate the presence of a malignant cardiac rhythm that is monomorphic ventricular tachycardia.

16. The implantable medical device of claim 11 wherein the operational circuitry is configured such that the first result is generated from a measure of interval rate stability, and if the first result indicates that the interval rate stability is outside of plus/minus 30 milliseconds, the first result is found to unambiguously indicate the presence of a malignant cardiac rhythm that is one of polymorphic ventricular tachycardia, or ventricular fibrillation.

17. The device of claim 11 wherein the operational circuitry is housed in a canister along with a battery and high voltage circuitry for delivery of electrical defibrillation or cardioversion therapy, the canister being adapted to receive a lead having a plurality of electrodes thereon, such that the first, second and third electrodes comprise at least one electrode on the canister and at least one electrode on a lead.

18. The device of claim 17 wherein the operational circuitry is configured to deliver defibrillation therapy in response to identification of a malignant arrhythmia, and to withhold defibrillation therapy if a non-malignant cardiac rhythm is identified.

19. An implantable medical device system comprising the device of claim 17 and an implantable lead having a plurality of electrodes thereon.

20. An implantable medical device comprising operational circuitry configured to receive cardiac electrical signals from at least first, second and third implantable electrodes such that at least first and second sensing vectors for sensing cardiac electrical signals are available to the operational circuitry, wherein the operational circuitry is configured to analyze cardiac activity in order to identify an arrhythmia as follows:
  observe a signal metric of the signals captured by at least the first and second sensing vectors;
  select a default sensing vector among the at least first and second sensing vectors for use in cardiac signal analysis;
  analyze a first signal captured from the default electrode pair;
  determine whether: a normal sinus rhythm has been sensed, an arrhythmia has been sensed, or ambiguity is present; and
  if ambiguity is present, analyze a second signal captured from a different one of the at least first and second sensing vectors to resolve the ambiguity.

* * * * *